(12) United States Patent
Bengtsson et al.

(10) Patent No.: US 10,232,121 B2
(45) Date of Patent: Mar. 19, 2019

(54) INJECTION DEVICE HAVING AUTOMATIC NEEDLE RETRACTION

(71) Applicant: Novo Nordisk A/S, Bagsvaerd (DK)

(72) Inventors: Henrik Bengtsson, Taastrup (DK); Ronan Carroll, Tisvildeleje (DK)

(73) Assignee: Novo Nordisk A/S, Bagsvaerd (DK)

(*) Notice: Subject to any disclaimer, the term of this patent is extended or adjusted under 35 U.S.C. 154(b) by 64 days.

(21) Appl. No.: 15/126,666

(22) PCT Filed: Mar. 16, 2015

(86) PCT No.: PCT/EP2015/055390
§ 371 (c)(1),
(2) Date: Sep. 16, 2016

(87) PCT Pub. No.: WO2015/140086
PCT Pub. Date: Sep. 24, 2015

(65) Prior Publication Data
US 2017/0087306 A1 Mar. 30, 2017

(30) Foreign Application Priority Data
Mar. 21, 2014 (EP) .................................. 14160992

(51) Int. Cl.
*A61M 5/31* (2006.01)
*A61M 5/315* (2006.01)
(Continued)

(52) U.S. Cl.
CPC ...... *A61M 5/31551* (2013.01); *A61M 5/2466* (2013.01); *A61M 5/31536* (2013.01);
(Continued)

(58) Field of Classification Search
CPC .. A61M 2005/2444; A61M 2005/3118; A61M 2005/3126; A61M 5/2466;
(Continued)

(56) References Cited

U.S. PATENT DOCUMENTS

| | | | |
|---|---|---|---|
| 2015/0174335 A1* | 6/2015 | Roervig | A61M 5/20 604/198 |
| 2015/0202365 A1* | 7/2015 | Roervig | A61M 5/20 604/198 |
| 2015/0273161 A1* | 10/2015 | Bengtsson | A61M 5/001 604/198 |

FOREIGN PATENT DOCUMENTS

| | | |
|---|---|---|
| WO | 03/045480 | 7/2003 |
| WO | 2008/077706 A1 | 7/2008 |
| WO | 2012025639 A1 | 3/2012 |

* cited by examiner

*Primary Examiner* — Imani Hayman
(74) *Attorney, Agent, or Firm* — Wesley Nicolas (57) ABSTRACT

The present invention relates to an injection device for delivering set doses of a liquid drug to a user. The injection device has a scale drum for displaying the set dose, which scale drum is helically guided in a housing. The scale drum is thus rotational in relation to the housing between a zero position and a set position for displaying the set dose. Further, a needle cannula secured to a hub is mounted in an axially movable manner. The axial movement of the hub is generated by a spring. A blocking mechanism interacting between the scale drum and hub controls the axial movement of the hub such that the needle cannula automatically retracts from the skin of a user in response to the scale drum reaching the zero position.

12 Claims, 8 Drawing Sheets

(51) Int. Cl.
*A61M 5/32* (2006.01)
*A61M 5/24* (2006.01)
*A61M 5/20* (2006.01)

(52) U.S. Cl.
CPC ...... *A61M 5/31581* (2013.01); *A61M 5/3204* (2013.01); *A61M 5/326* (2013.01); *A61M 5/3293* (2013.01); *A61M 2005/206* (2013.01); *A61M 2005/2444* (2013.01); *A61M 2005/3118* (2013.01); *A61M 2005/3126* (2013.01); *A61M 2005/3267* (2013.01)

(58) Field of Classification Search
CPC .......... A61M 5/31536; A61M 5/31551; A61M 5/31581; A61M 5/3204; A61M 5/3293
See application file for complete search history.

Fig. 14   Skin   Fig. 15

INJECTION DEVICE HAVING AUTOMATIC NEEDLE RETRACTION

CROSS-REFERENCE TO RELATED APPLICATIONS

This application is a 35 U.S.C. § 371 National Stage application of International Application PCT/EP2015/055390 (published as WO2015/140086), filed Mar. 16, 2015, which claims priority to European Patent Application 14160992.5, filed Mar. 21, 2014; the contents of which are incorporated herein by reference.

THE TECHNICAL FIELD OF THE INVENTION

The invention relates to an injection device with automatic retraction of the needle cannula after injection. The invention especially relates to such injection device in which the tip of the needle cannula is automatic removed from the skin of the user just before the entire dose has been delivered.

DESCRIPTION OF RELATED ART

Shielded needle assemblies are widely known. WO 2003/045480 discloses a safety needle assembly in which the axially movable shield locks after one injection such that the needle assembly cannot be reused.

WO 2008/077706 discloses a similar construction wherein the telescopic shield is prevented from axial movement when the needle assembly is removed from the injection device. However, every time the needle assembly is mounted onto the injection device the shield unlocks.

DESCRIPTION OF THE INVENTION

It is an object of the present invention to provide an injection device in which the flow through the needle cannula is interrupted just before the full dose has been delivered.

The invention is defined in the attached claim 1 followed by a number of embodiments. The individual claims are explained in details in the following.

The invention lies in a mechanism which retracts the tip of the needle cannula from the skin of the user immediately before, or in the same moment as the full dose has been injected. Since injection devices of the type where a user can select or set a dose usually comprises a scale drum for displaying the set dose such retraction mechanism comprises means for retracting the tip of the needle cannula in response to the scale drum reaching its zero position. "In response" can mean either upon reaching the zero position or immediately before reaching the zero position.

The "zero position" of the scale drum is the position in which no dose is set and a zero is indicated to the user, preferably by having the indicia "0" appear in a window as it is generally known from injection devices. The zero position occurs both initially when the injection device is taken into use and also at the end of an injection where the scale drum is automatically returned to the zero position.

Accordingly, in one aspect of the present invention, the injection device comprises:

A housing provided with a thread guiding a scale drum. The housing further secures a cartridge containing the liquid drug to be ejected. The thread guides the scale drum such that the scale drum is moved helically away from the zero position during dose setting and returned helically to the zero position during dose expelling. The threads provided in the housing is preferably provided on an inside wall of the housing or alternatively on the outer surface of a tower erected internally in the housing.

The injection apparatus further comprises a needle cannula having a proximal part for penetrating into the cartridge and a distal part having a tip for penetrating the skin of a user. The needle cannula is mounted in a hub which is telescopically movable in relation to the cartridge. The distal part or at least the tip of the needle cannula is covered, at least longitudinal by a telescopic movable shield which is axial movable in relation to the housing between an extended position and a retracted position and which shield is urged in the extended direction by a first spring encompassed between the housing and the shield.

A second spring is provided between the shield and the hub which second spring automatically move the hub in a proximal direction once the hub is set free to slide.

Further a blocking mechanism interact between the scale drum and the hub such that the blocking mechanism prevents axial movement of the hub and thus the needle cannula when the scale drum is rotated away from the zero position and allow axial movement when the scale drum is in the zero position.

When a dose is set i.e. when the scale drum is rotated away from the zero position, the blocking mechanism blocks any proximal movement of the hub and thus the needle cannula. In this position the hub is locked relatively to the housing and the shield operates as a usual safety shield covering the tip of the needle cannula.

Whenever the scale drum reaches the zero position, the blocking mechanism is set free to move axially. As the blocking mechanism is released in this zero position, the hub and the needle cannula can now move axially. It is thus possible for the spring encompassed between the shield and the hub to move the hub in the proximal direction and thus remove the needle from the skin of the user.

The proximal movement of the hub and thus the needle cannula occurs instantly when the scale drum reaches the zero position following an injection cycle such that the needle cannula is automatically pulled out of the skin of the user when the injection devices reaches the zero position. When the hub is pushed proximally by the spring at the end of the injection cycle, the shield is usually in the retracted position which the shield normally always is at the end of an injection cycle simply because the shield is pressed in the proximal direction by the skin of the user during injection.

Since the needle cannula is removed from the skin at the same moment the scale drum reaches the zero position a slight overpressure will remain in the cartridge. In a further embodiment wherein the tip of the needle cannula is contained in a cleaning chamber this slight overpressure will be distributed between the interior of the cartridge and the cleaning chamber.

The blocking mechanism further comprises at least a first element and a second element:

The first element is rotatable secured to the housing and can only rotate relative to the housing i.e. it is axially secured to the housing. This first element is preferably operated by the scale drum such that the scale drum rotates the first element.

The second element is axially movable and coupled to the hub to follow axial movement of the hub. In one solution, the second element and the hub can be made as one unisome element.

The axial movement of the second element and thus axial movement of the hub are controlled by the first element which is rotatable between a first position and a second position by the helically movable scale drum;

In the first position both the second element and the hub is prevented from moving axially in a proximal direction, such that the axial position of the hub and thus the needle cannula is locked in relation to the housing.

In the second position both the second element and the hub is axially movable in a proximal direction, such that the needle cannula secured in the hub is also axially movable in relation to the housing, The shift from the first position to the second position is commanded by the scale drum abutting the first element. Just before the scale drum reaches its zero position, it abuts the first element which is thus rotated out of its engagement with the second element which is thereby set free to move axially.

The second element and the hub are thereby freely movable in an axial direction when the scale drum approaches its zero position as well as in the second position whereas once a dose has been set and the scale drum is rotated away from its zero position, the second element and the hub is locked and prevented from axial movement relatively to the housing.

Once the scale drum rotates the first element away from its engagement with the second element i.e. when reaching the zero position, the second spring operates the second element together with the hub in a proximal direction. Since the needle cannula is mounted in the hub this axial movement of the hub also moves the needle cannula including the tip proximally. As the tip is moved proximally it will also be moved into a position in which means for interrupting the flow through the lumen of the needle cannula can be provided.

When no dose is set i.e. when the scale drum is in its zero position, both the hub and the second element is free to move axially. Since the hub can slide in relation to the cartridge movement of the shield in this position is via the first spring transformed into axial movement of the hub with the result that the distal part of the needle cannula move further into the interior of the cartridge. This happens because the stiffness of this second spring is relatively high.

During injection both the first spring and the second spring is compressed since the hub is maintained in its locked position and the shield is retracted. Following injection, when the scale drum approaches its zero position, the shield is still retracted and the second spring pushes the hub proximally moving the tip of the needle cannula out from the skin of the user.

The injection device is further provided with means for interrupting the flow through the lumen of the needle cannula as the tip is removed from the skin of the user.

These means can be any kind of valve which in a simple form can be a solid rubber piece carried by the shield in which solid part the tip of the needle cannula is parked when retracted from the skin. The important feature being that the lumen is sealed off such that an overpressure can be maintained inside the interior of the cartridge.

In a preferred embodiment these means is provided as a cleaning reservoir into which the tip of the needle cannula is retracted just before the zero position is reached. The result being that the overpressure will remain inside the cartridge and the cleaning chamber as it cannot escape through the needle cannula since the tip is submerged into the cleaning solvent of the cleaning reservoir. The cleaning solvent entrapped in the reservoir can be any kind of anti-bacterial solvent. In a preferred embodiment, this cleaning solvent is the drug contained in the cartridge as described in International patent application No.: PCT/EP2014/071746. This has the benefit that the drug contained in the cartridge is not contaminated by the cleaning solvent as it is the same liquid. Since a liquid drug usually contains one or more antibacterial additives, e.g. preservatives as phenol or metacresol, these additives will also keep the tip of the needle cannula clean between subsequent injections.

The reservoir is preferably provided with a proximal septum and a distal septum made from a rubber material pierceable by the needle cannula.

The shifting between the two positions of the first element is preferably done by the scale drum. In the second position i.e. the zero position of the scale drum, the scale drum urges the first element out of engagement with the second element. This happens against the force of a radially working spring mounted between the first element and the housing. In the first position when a dose is set, this radially working spring urges the first element back into its engaging position i.e. the position in which the second element and the hub is prevented from axial movement.

The first element is preferably constructed as a ring-shaped body having a distal extension and a proximal extension. This ring-shaped element is preferably rotatable guided in a track provided internally in the housing. The distal extension preferably abut the second element in the first position whereas the scale drum abuts the proximal extension in the second position thus rotating the ring shaped-element and thereby the proximal extension out of engagement with the second element.

The shield is preferably axially guided in a track provided internally in the housing such that the shield can telescope in relation to the housing. The hub, which is also telescopic in relation to the housing, is distally provided with a radially extending flange which engages a recess provided in the shield such that the hub is pulled in the distal direction by the shield following an injection.

Definitions:

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle units specially designed for pen injections systems are defined in ISO standard No. 11608, part 2, and are often referred to as "pen needles". Pen needles have a front-end for penetrating into the user and a back-end for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing. The Arabian number "0" is usually visible in the window when the scale drum is in the "zero position", which indicates that no dose has been set, or that the set dose has been ejected and the scale drum automatically has returned to the zero position with no dose being set.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

The term "Permanently connected" as used in this description is intended to mean that the parts, which in this application is embodied as a cartridge and a needle assembly, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise"

and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula supposed to be inserted into the skin of the user whereas the term "proximal end" is meant to refer to the opposite end pointing away from the user during injection.

Figures 2, 3:
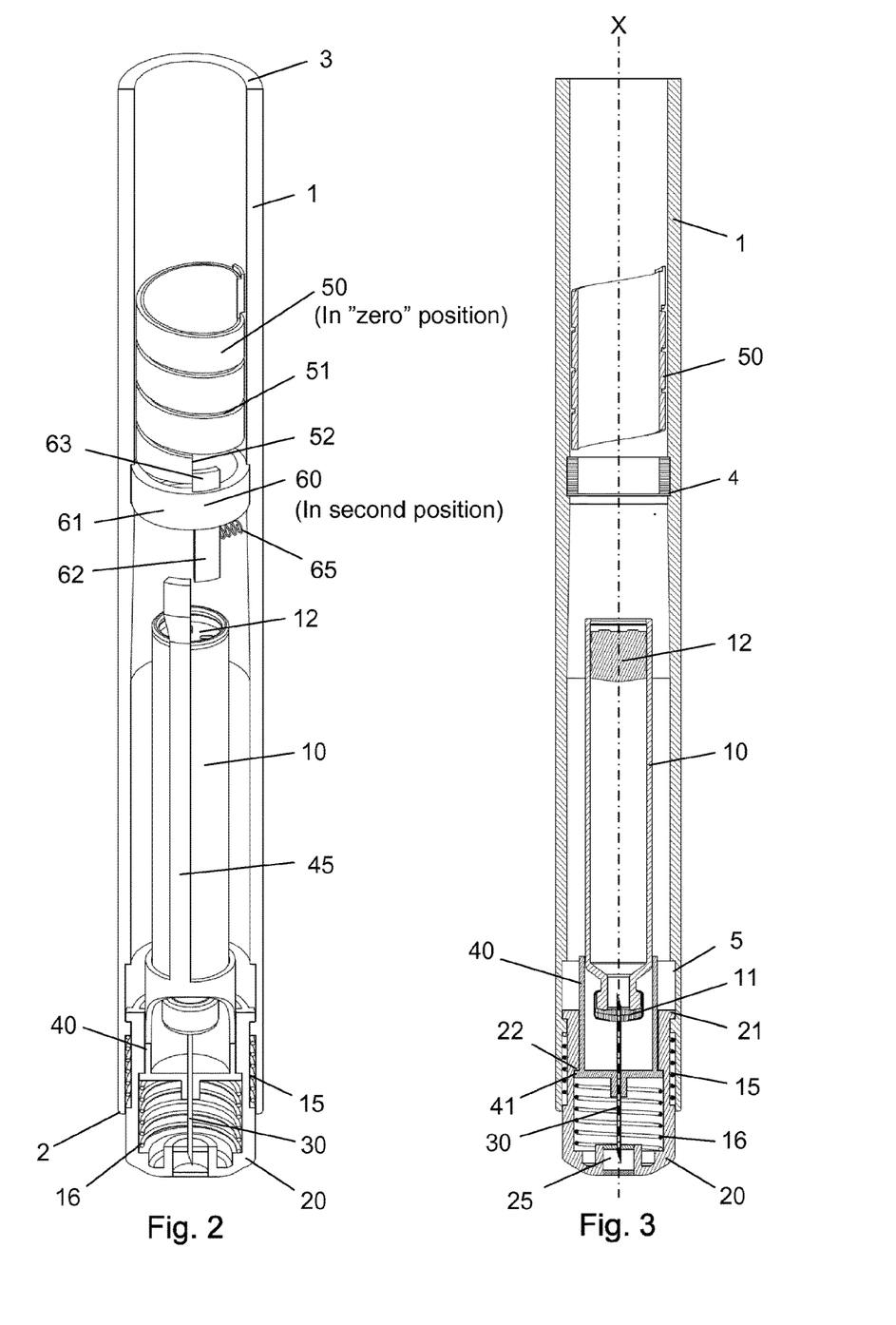
FIG. 2-3 shows the injection device with the scale drum in the zero position and ready for dose setting.

Further, as indicated in FIG. 3, the axis "X" is the longitudinal centre axis of the injection device defining the axial direction of the injection device.

The injection device as depicted in FIGS. 1 to 15 comprises:

A housing 1 having a distal end 2 and a proximal end 3. The housing 1 further secures a cartridge 10 containing a liquid drug.

A telescopic shield 20 which is secured to the distal end 2 of the housing 1 and axially movable between an extended position and a retracted position.

A first axial spring 15 encompassed between the housing 1 and the shield 20 and urging the shield 20 into the extended position. This first axial spring 15 preferably rest on a flange in the housing 1 and a similar flange provided on the shield 20.

A needle cannula 30 secured to a hub 40. The hub 40 is axially movable in relation to the housing 1 and thus the cartridge 10 and relatively to the shield 20.

A second axial spring 16 provided between the distal surface of the hub 40 and the shield 20.

Proximally the housing 1 is provided with an internal thread which carries a scale drum 50. The scale drum 50 has an external helical thread 51 and is coupled to a not-shown dose setting mechanism such that the scale drum 50 rotate proximally during dose setting. The resulting movement of the scale drum 50 thus being helically. The scale drum 50 is preferably rotatable in both directions of rotation such that any set dose can also be decreased.

A blocking mechanism comprising a first element 60 and a second element 45.

The first element 60 being rotatable secured in a track 4 in the housing 1 such that the first element 60 can rotate relatively to the housing 1 but is axially locked in relation to the housing 1.

The second element 45 is distally coupled to the hub 40 to follow axial movement of the hub 40 and proximally blocked in its proximal movement by the first element 60. In the disclosed embodiment, the hub 40 and the second element 45 is moulded as one unitary component, but it could easily be made as two separate parts.

Figure 1:
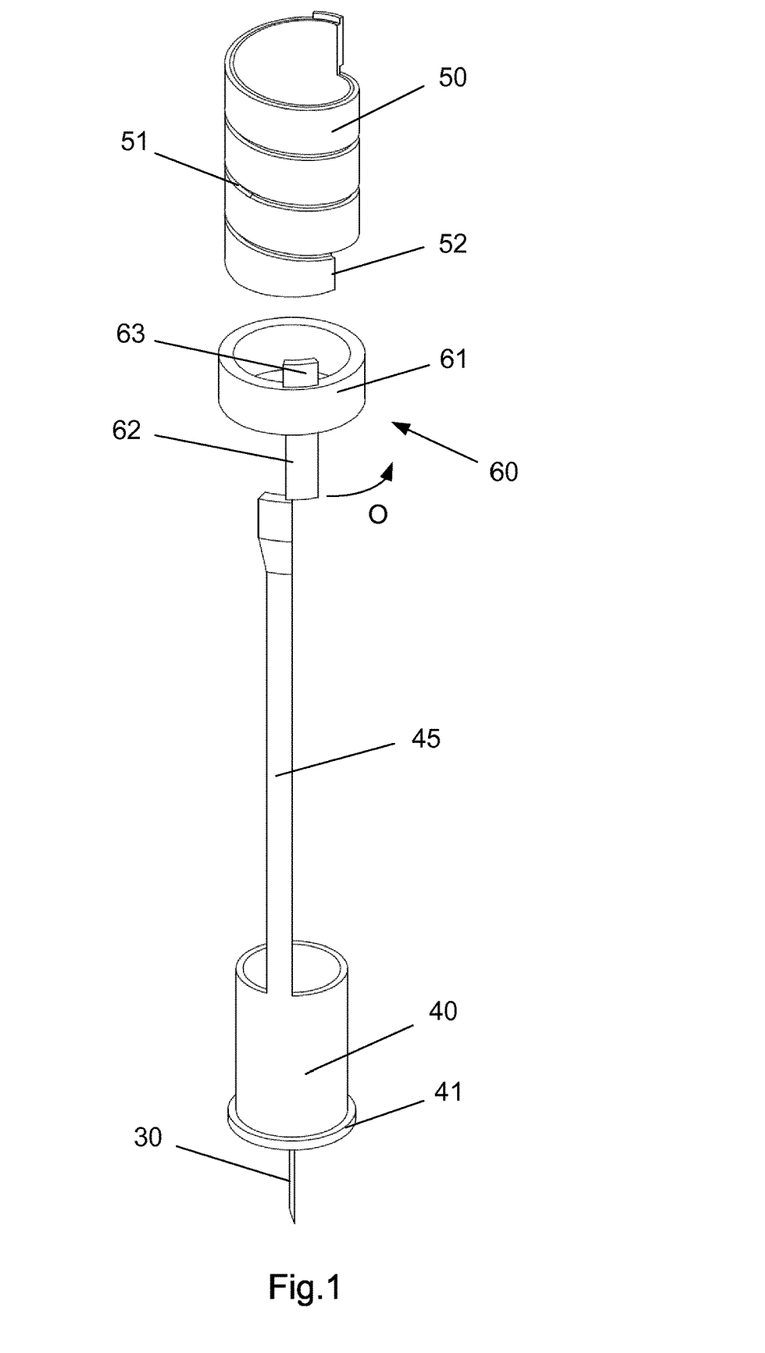
FIG. 1 shows the working principle of the invention

FIG. 1 discloses the first element 60 of the blocking mechanism, the hub 40 and the second element 45 formed as one unitary element and the scale drum 50.

As the first element 60 is rotated it can either block axial movement of the second element as disclosed in FIG. 1 or allow such axial movement when rotated further in an anti-clockwise direction (when viewed from the proximal end 3 of the housing 1) as indicated by the arrow "O" in FIG. 1.

The scale drum 50 is configured as a traditional hollow scale drum 50 which has a helical thread 51 guided in a thread or thread segment provided internally in the housing 1.

Figures 4, 5:
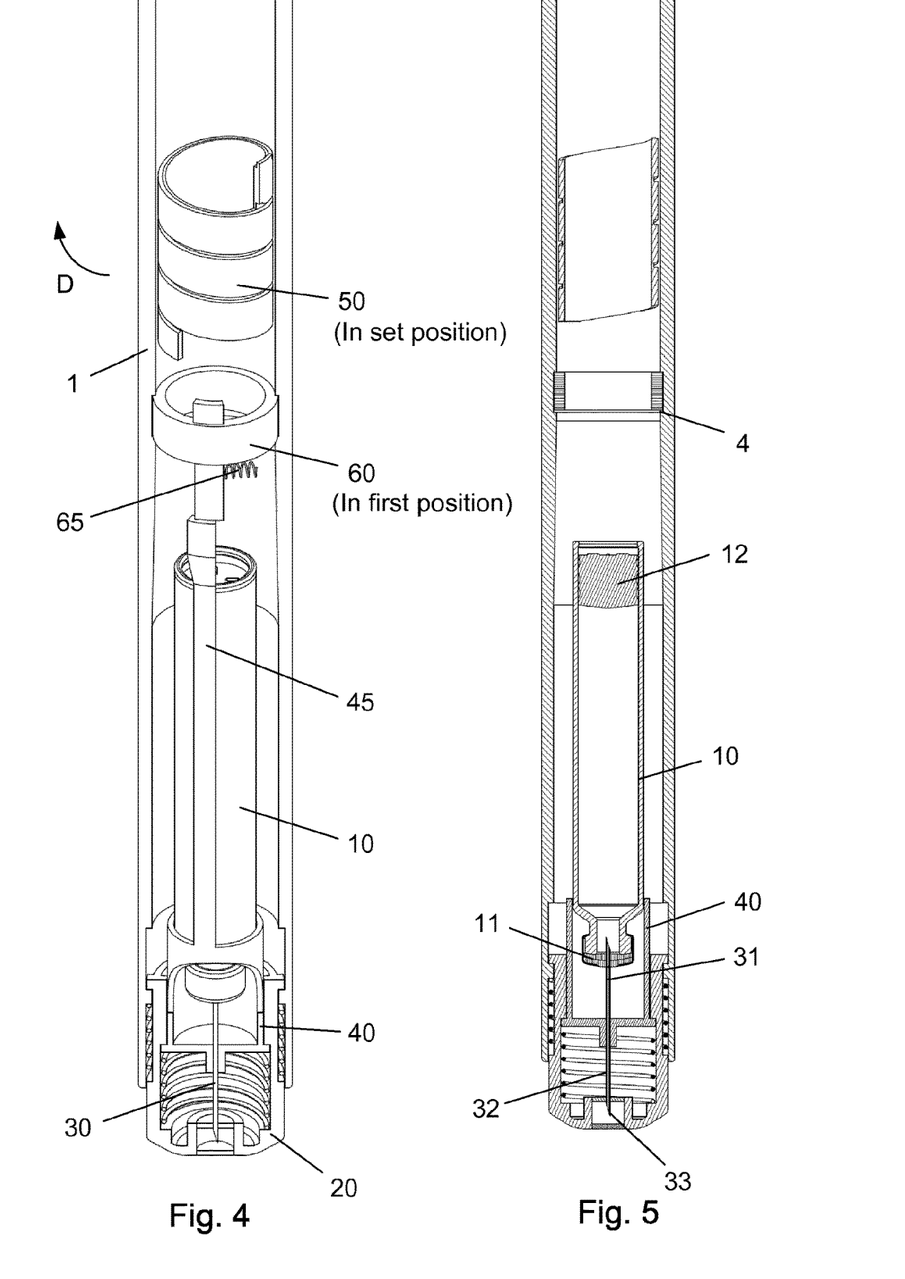
FIG. 4-5 shows the injection device as a dose is being dialed.

The first element 60 comprises a circular ring 61 which is guided in a circular track 4 in the housing (see e.g. FIG. 3). The circular ring 61 of the first element 60 further has a distal extension 62 and a proximal extension 63. The first element 60 is rotatable between a first position and a second position. The first position is depicted in FIG. 4 and the second position is shown in FIG. 2. In the first position as depicted in FIG. 4, the first element 60 block the proximal movement of the second element 45. In the second position of FIG. 2, the second element 45 is movable in the proximal direction. A radially working spring 65 is provided between the first element 60 and the housing 1 for rotatable urging the first element 60 into the first position.

Further, the scale drum 50 has a distal end surface 52 which abut the proximal extension 63 on the first element 60 when the scale drum 50 is in a "zero" position. The result being that the second element 45 is only movable in the proximal direction when the scale drum 50 is in its "zero" position. The "zero" position as depicted in FIG. 2-3 is the position in which no dose has been set by the user. The scale drum 50 usually carries indicia showing the size of the dose through a window in the housing 1.

As indicated in e.g. FIG. 5, the needle cannula 30 is secured to the hub 40 and has a proximal end 31 for penetrating into the cartridge 10 and a distal part 32 having a sharp tip 33 for penetrating the skin of the user.

The cartridge 10 is secured in the housing 1 such that the cartridge 10 cannot move axially in relation to the housing 1. The cartridge 10 contains the liquid drug to be injected and is distally provided with a septum 11 which is pierced by the proximal part 31 of the needle cannula 30. The proximal end of the cartridge 10 is sealed by a movable plunger 12 which is moved forward during injection in accordance with the size of the set dose indicated on the scale drum 50.

As depicted in FIG. 3, the housing 1 is further provided with a longitudinal track 5 in which a protrusion 21 provided on the shield 20 is guided. Both the track 5 and the protrusion 21 can as disclosed be formed 360 degrees around the injection device. Further, the shield 20 can be provided with a recess 22 in abutment with a radial flange 41 on the hub 40.

Initially prior to performing an injection, as disclosed in FIG. 2-3, the scale drum 50 is positioned in its zero position and the distal end surface 52 of the scale drum 50 abut the proximal extension 63 on the first element 60. This rotates the first element 60 radially against the force of the radially working spring 65 and out of engagement with the second element 45. In this second position of the first element 60, the second element 45 and the hub 40 are both movable in an axial direction. Should a user move the shield 20 proximally this movement will also, via the second spring 16, move the hub 40 and the second element 45 proximally. The second spring 16 preferably has a stiffness sufficient to transform axial movement of the shield 20 into axial movement of the hub 40 such that proximal movement of the hub 40 in this position would move the proximal part 31 of the needle cannula 30 further into the interior of the cartridge 10 (similar to the situation depicted in FIG. 13). The tip 33 of the needle cannula 30 is therefore not exposed in this initial position, not even if the shield 20 is pressed proximally.

When setting a dose as disclosed in FIG. 4-5, the scale drum 50 and thus the distal end surface 52 thereof is rotated helically away from its zero position. This is indicated by the arrow "D". The radial spring 65 thus rotates the first element 60 and the proximal extension 63 thereon into its first position in which the second element 45 is prevented from moving in the proximal direction. The proximal end of the second element 45 abuts the distal extension 62 on the first element 60. This also hinders the hub 40 from moving proximally. The tip 33 of the needle cannula 30 is thus locked in position relatively to the telescopic shield 20.

Figure 6:
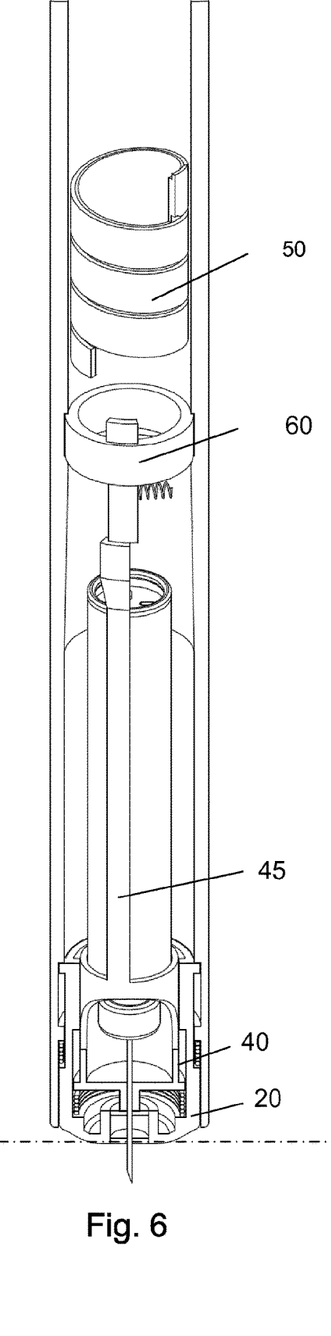
FIG. 6-7 shows the injection device with the tip of the needle cannula inserted through the skin of a user.
Figure 7:
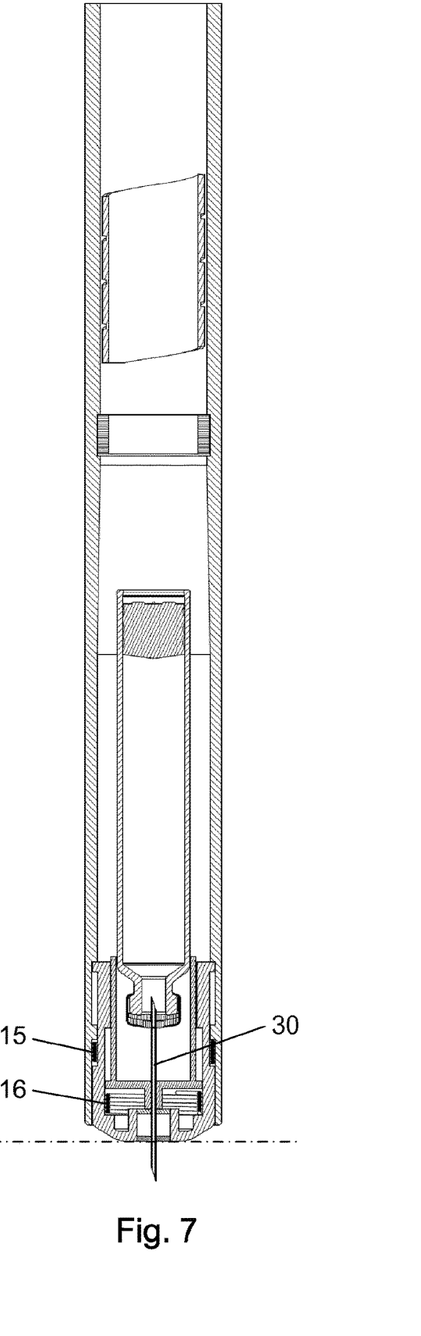

Once a dose has been selected, the user presses the distal surface of the shield 20 against the skin as disclosed in FIG. 6-7. The surface of the skin is indicated by a dotted line. Since the hub 40 is locked in its axial position this proximal movement of the shield 20 compresses both the first spring 15 provided between the housing 1 and the shield 20 and the second spring 16 encompassed between the hub 40 and shield 20. The shield 20 thus moves proximally whereas the hub 40 remains in its locked position and the distal part 32 of the needle cannula 30 penetrates the skin.

Figure 8:
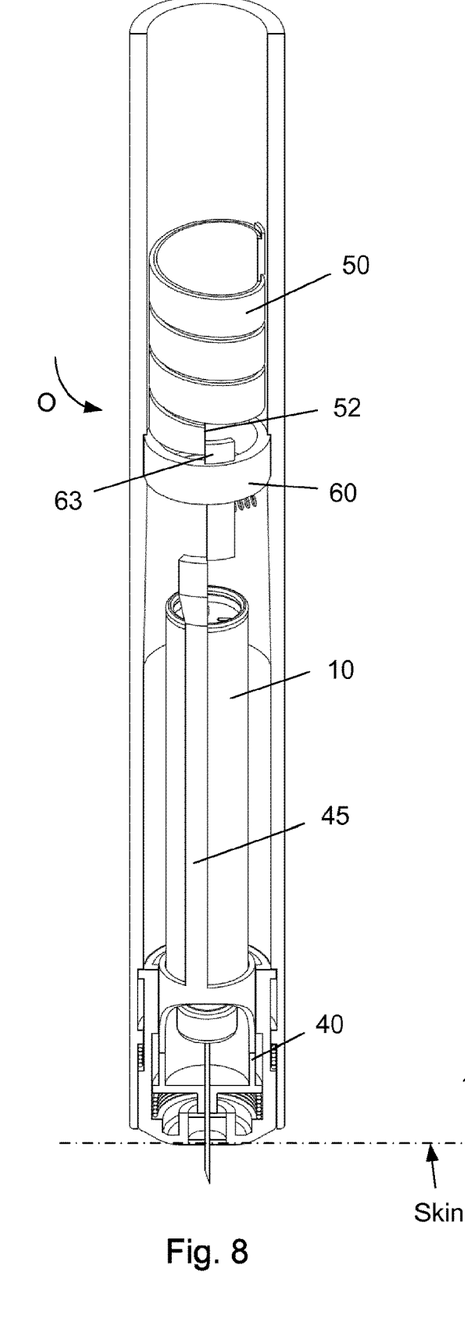
FIG. 8-9 shows the injection device performing an injection.
Figure 9:
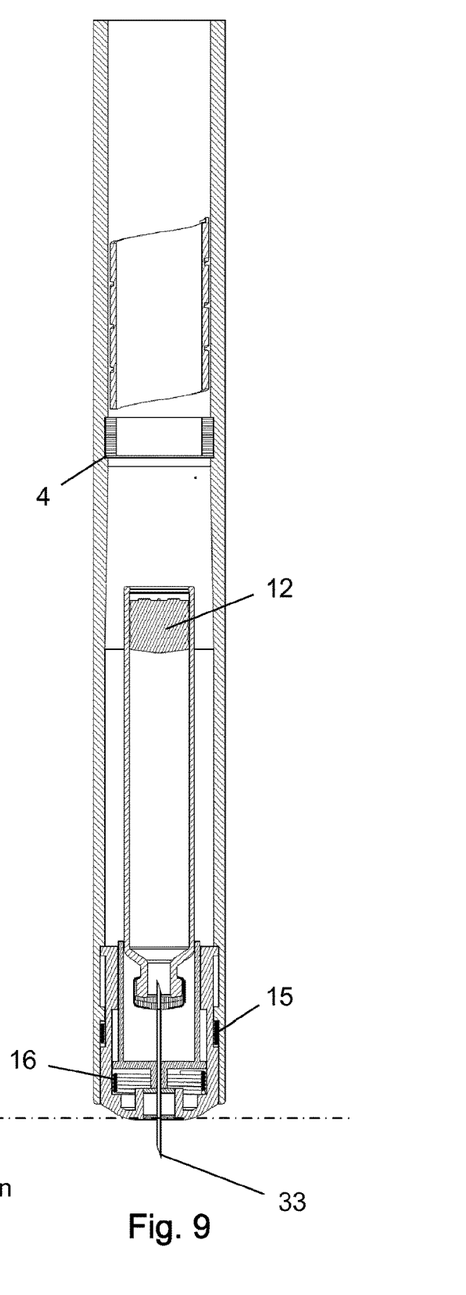

With the tip 33 of the needle cannula 30 inserted into the skin of the user, the set dose is now released as disclosed in FIG. 8-9. The injection is preferably done automatically by a spring engine which urges the plunger 12 forward inside the cartridge 10 to expel the set dose. Simultaneously, the scale drum 50 is rotated back towards its zero position. This is indicated by the arrow "O" in FIG. 8. FIG. 8-9 depictures the situation as the scale drum 50 approaches its zero position. The first element 60 start to rotate against the force of the radial spring 65 as the scale drum 50 approaches its zero position and the distal end surface 52 of the scale drum 50 starts pushing on the proximal extension 63 on the first element 60.

Figure 10:
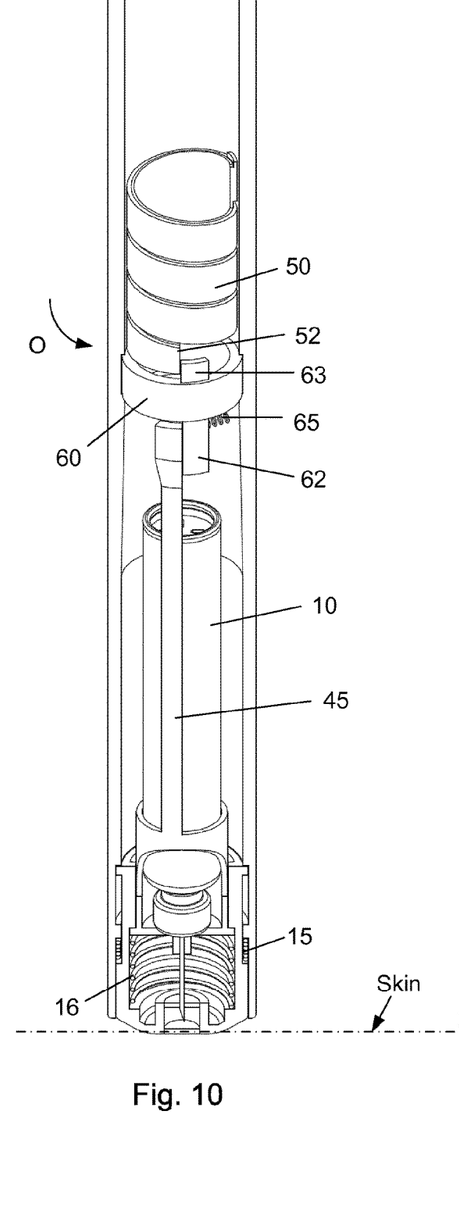
FIG. 10-11 shows the injection device just before the scale drum returns to its zero position.
Figure 11:
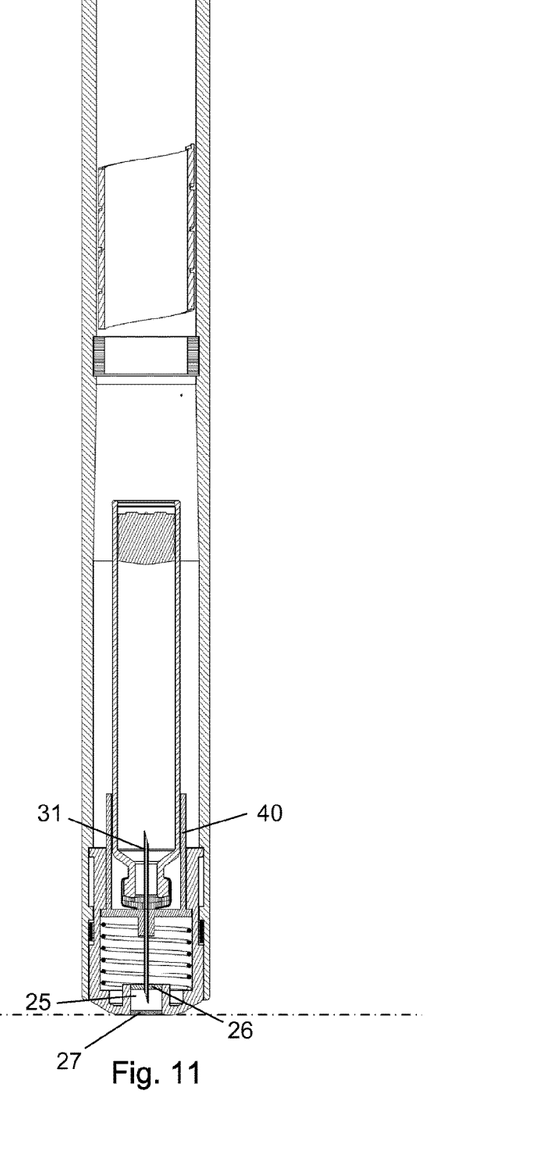

Once the scale drum 50 is about to reach its zero position as depicted in FIG. 10-11, the proximal extension 63 and especially the distal extension 62 of the first element 60 is rotated out of its blocking engagement with the second element 45. Since the shield 20 is still pressed against the skin of the user, the second spring 16 encompassed between the hub 40 and the shield 20 urges the hub 40 in the proximal direction. This proximal movement of the hub 40 also retracts the tip 33 of the needle cannula 30 from the skin of user.

The blocking mechanism is preferably made such that the tip 33 of the needle cannula 30 is pulled out from the skin of the user just before the scale drum 50, and thereby the injection device, reaches its zero position.

As disclosed in the figures the shield 20 is distally provided with a cleaning reservoir 25 which is situated between a distal septum 26 and a proximal septum 27. Between injections, the tip 33 of the needle cannula 30 is maintained submerged in a cleaning solvent contained in this cleaning reservoir 25. The cleaning solvent is preferably the drug contained in the cartridge 10 as described in International patent application No.: PCT/EP2014/071746.

As depicted in FIG. 10-11, the tip 33 of the needle cannula 30 is retracted into the cleaning reservoir 25 right before the scale drum 50 rotates into its zero position. In this position a slight overpressure will be maintained inside the cartridge 10 since the overpressure cannot escape since the tip 33 is submerged in the cleaning solvent.

Figure 12:
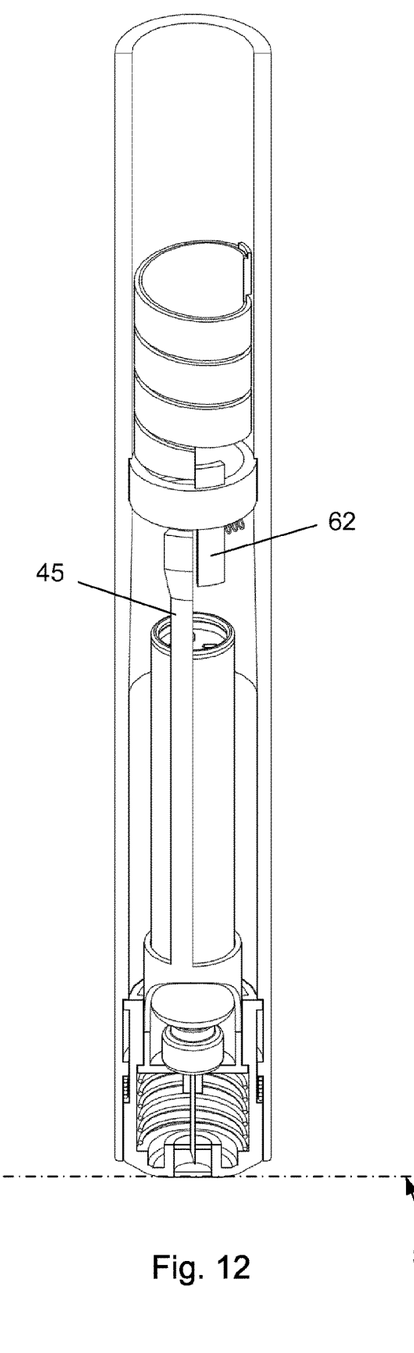
FIG. 12-13 shows the injection device with the scale drum in its zero position.
Figure 13:
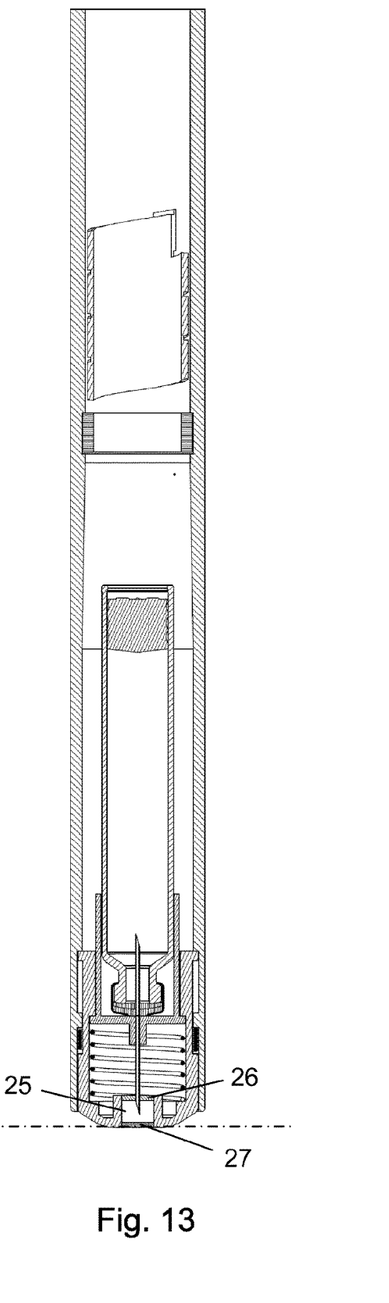

In FIG. 12-13, the scale drum 50 has reached its zero position which has moved the proximal extension 63 on the first element 60 further in its rotational movement such that a slight air-gap is now established between the distal end of the second element 45 and the distal extension 62 on the first element 60.

Figure 14:
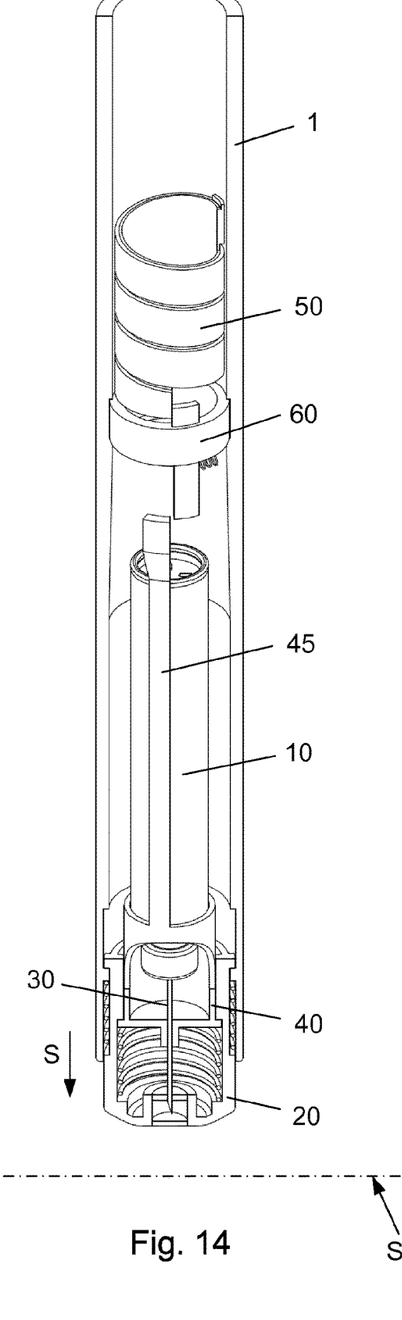
FIG. 14-15 shows the injection device with the scale drum in its zero position and removed from the skin of the user.
Figure 15:
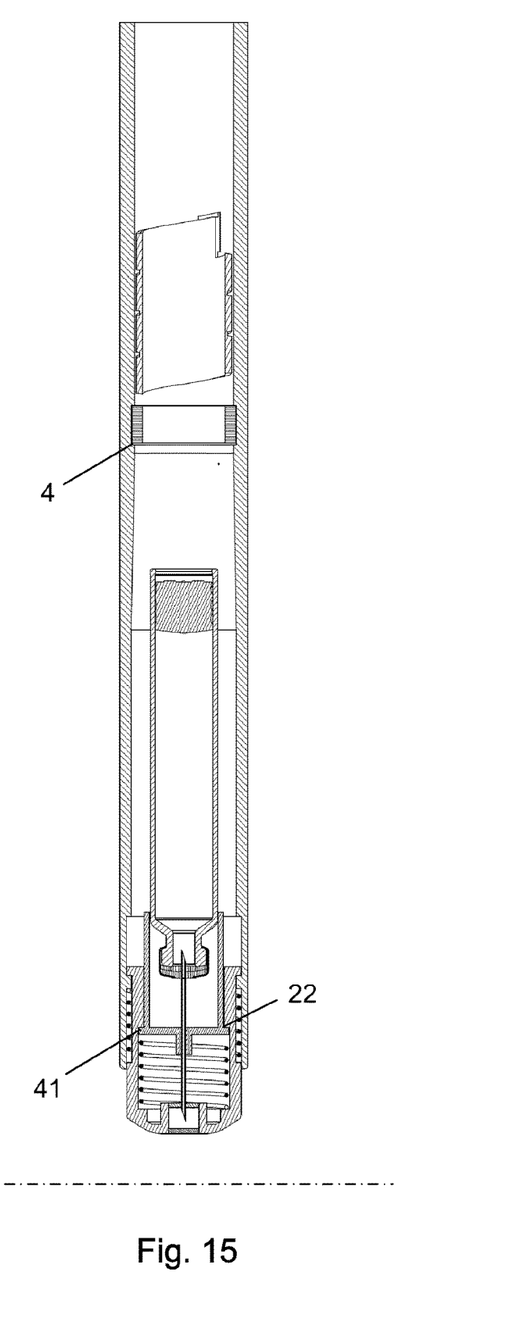

When the distal end of the shield 20 is removed from the skin of the user as disclosed in FIG. 14-15, the second spring 16 urges the shield 20 in the distal direction as indicated by the arrow "S". This also pulls the hub 40 in the distal direction since the internal recess 22 on the shield 20 engages a similar radial flange 41 on the hub 40. The injection device is now in its state-of-rest as also disclosed in FIG. 2-3.

Some preferred embodiments have been shown in the foregoing, but it should be stressed that the invention is not limited to these, but may be embodied in other ways within the subject matter defined in the following claims.

The invention claimed is:

1. An injection device for delivering set doses of a liquid drug comprising:
    a housing having a longitudinal axis (X) and provided with a thread, and axially securing a cartridge containing the liquid drug to be expelled,
    a rotatable scale drum for displaying a size of the set dose, the scale drum is rotatable between a zero position and a set position, the scale drum engaging the thread of the housing such that the scale drum is moved helically away from the zero position during dose setting and returned helically to the zero position during dose expelling,
    a needle cannula adapted to be mounted to the injection device and comprising a distal part with a distal tip for penetrating skin of a user and a proximal part for penetrating into the cartridge and the needle cannula is secured in a hub which is telescopically movable along the longitudinal axis (X),
    a slidable shield axially movable in relation to the housing along the longitudinal axis (X) between an extended position covering at least the distal tip of the needle cannula and a retracted position and the shield further is urged in the extended direction by a first spring encompassed between the housing and the shield,
    a second spring encompassed between the shield and the hub, and
    a blocking mechanism interacting between the scale drum and the hub, wherein the blocking mechanism prevents axial movement of the hub when the scale drum is rotated away from the zero position and allow axial movement when the scale drum is in the zero position.

2. The injection device according to claim 1, wherein the blocking mechanism comprises a first element and a second element;
    the first element being rotatable secured to the housing such that the first element can only rotate relative to the housing, and
    the second element being axially movable along the axis (X) and coupled to the hub to follow axial movement of the hub.

3. The injection device according to claim 2, wherein the first element is rotated between a first position and a second position by the rotatable scale drum;
    the first position being a position in which the second element and the hub is prevented from telescopically movement in a proximal direction, such that the axial position of the hub is locked in relation to the housing,
    the second position being a position in which the second element and the hub is telescopically movable in a proximal direction, such that the hub is axially movable in relation to the housing.

4. The injection device according to claim 3, wherein the shield distally carries a cleaning reservoir for cleaning at least the distal tip of the needle cannula between injections.

5. The injection device according to claim 4, wherein the shield is axially guided in a track in the housing.

6. The injection device according to claim 5, wherein the hub is provided with a radial flange engaging a recess provided in the shield.

7. The injection device according to claim 4, wherein the cleaning reservoir proximally has a barrier in form of a proximal septum and distally has barrier in form of a distal septum.

8. The injection device according to claim 2, wherein the hub and the second element is formed as one unitary part.

9. The injection device according to claim 2, wherein the first element is urged into the first position by a radially working spring.

10. The injection device according to claim 2, wherein the first element is urged into a second position by the scale drum.

11. The injection device according to claim 2, wherein the first element is provided with a ring-shaped body and a distal extension and a proximal extension.

12. The injection device according to claim 11, wherein the proximal extension abuts a distal end surface of the scale drum in the second position.

* * * * *